United States Patent [19]
Gorun et al.

[11] Patent Number: 5,627,164
[45] Date of Patent: May 6, 1997

[54] PYRAZOLYL BORATES COMPLEXES-(LAW294)

[75] Inventors: Sergiu M. Gorun, Upper Montclair; Robert T. Stibrany, Long Valley, both of N.J.

[73] Assignee: Exxon Research and Engineering Company, Florham Park, N.J.

[21] Appl. No.: 489,860

[22] Filed: Jun. 13, 1995

[51] Int. Cl.$^6$ ............................................ A61K 31/41
[52] U.S. Cl. .................................... 514/64; 548/110
[58] Field of Search ............................. 548/110; 514/64

[56] References Cited

PUBLICATIONS

CA 111:39575b A hydridovinyliridium . . . isomer. Ghosh et al., p. 621, 1989.
CA 112:152525q Boron–nitrogen . . . boranes. Komorowski et al. p. 793, 1990.
CA 122:44904q Isomerism . . . (NBD). Bucher et al., p. 1039 1995.

*Primary Examiner*—Joseph K. McKane
*Attorney, Agent, or Firm*—Joseph J. Dvorak

[57] ABSTRACT

Briefly stated, the present invention comprises a composition of matter having the formula $M_xL_yP_z \cdot nQ$ where M is a metal, P is a counterion, x, y, and z are integers, Q is a solvent, n is a numerical value of from 0 to about 12, and L is either a tris or a bis substituted pyrazolyl borate anion having the structural formula:

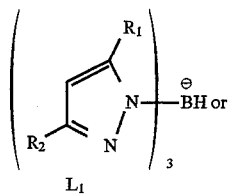

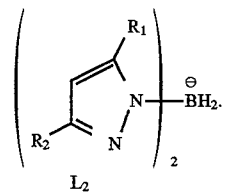

9 Claims, 2 Drawing Sheets

PYRAZOLYL BORATES COMPLEXES-(LAW294)

FIELD OF THE INVENTION

This invention relates a new class of compounds. More specifically, it relates to metal complexes having pyrazolyl borate ligands substituted with fluoroalky groups near the metal center.

BACKGROUND OF THE INVENTION

Pyrazolyl borates are a well known class of organic ligands, described most recently in several review articles: S. Trofimenko *Chem. Rev* 1993, 93, 943; S. Trofimenko *Prog. Inorg. Chem.* 1986, 34, 115. Metal complexes of organic ligands of the pyrazolyl borate class bearing mixed electron releasing-electron withdrawing substituents, like the trifluoromethyl group are rare. Only the K, Rh and Ir salts of hydrotris (3-(trifluoromethyl)-5-methylpyrazo-1-1-yl) borate, have been prepared and characterized. See C. K. Ghosh, J. K. Hoyano, R. Krentz, W. A. G. Graham, *J. Am. Chem. Soc.* 1989, 11 5480. Only K and Rh metal complexes of dihydro bis(3-(trifluoromethyl)-5-methylpyrazol-1-yl) borate, have been reported. See R. Krenz, Ph.D. Thesis, "Model Compounds in C—H Activation", University of Alberta, 1989).

SUMMARY OF THE INVENTION

The present invention comprises a composition of matter having the formula $M_xL_yP_z \cdot nQ$ where M is a metal ion, L is a fluoralkyl substituted bis or tris pyrazole borate anion, or a mixture thereof, P is a counterion, x, y, and z are integers sufficient to render the composition electrically neutral, Q is a solvent, and n is a numerical value of from 0 to about 12.

The metal complexes and especially the cobalt complex of the tris pyrazolyl borate anion are useful as oxidation catalysts.

DETAILED DESCRIPTION OF THE INVENTION

The compounds of the present invention have the formula $M_xL_yP_z \cdot nQ$ wherein M is a metal ion selected from transition and lanthanide metals; and L is a fluoroalkyl substituted tris or bis pyrazolyl borate anion, or mixture thereof; and P is a counterion, x, y and z are integers sufficient to render the composition electrically neutral; Q is a solvent, n is a numerical value of from 0 to about 12. In the composition of the present invention, the ligand L has the structure:

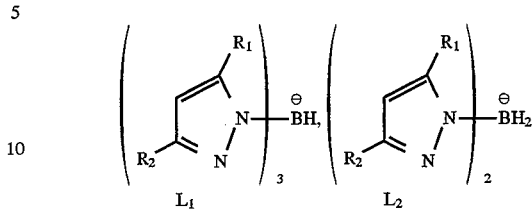

wherein $R_1$ is an alkyl group of from 1 to 12 carbon atoms or an aryl or aralkyl group of from 6 to 12 carbon atoms and $R_2$ is a fluoralkyl group of from 1 to 12 carbon atoms.

In the compositions of this invention preferably M is selected from the group consisting of Co, Ni, Zn, Mn, Cr, Zr, Ti, Hf, V, and Fe.

Typically, the counterion P will be selected from a halide, such as chloride or bromide, a nitrate, sulfate, a carboxylate of from about 1 to 12 carbon atoms, sulfonate, or borate, such as fluoroborate, and perchlorate.

Additionally, the solvent, Q, typically will be water, an alcohol of from about 1 to about 12 carbon atoms, acetonitrile, acetone, or any organic solvent in which the complex is soluble.

The compounds of the present invention are prepared by combining a solution of an alkali metal salt, especially the potassium salt of the ligands $L_1$ or $L_2$ having the formula:

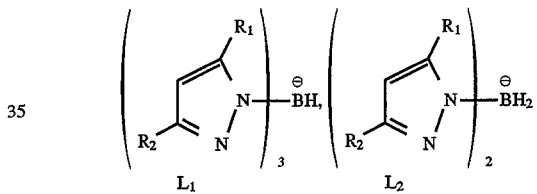

or mixtures of them, with a solution of a salt of the metal, M, where M is as previously defined: suitable salts of the metal, M, include chlorides, bromides, fluorides, nitrates, sulfates, alkyl or aryl sulfonates, fluoroborates, phenyl borates, perchlorates, and carboxylates. Suitable solvent include water, hydrocarbons, ketones (like acetone), nitriles, ethers, alcohols, dimethyl sulfoxide, dimethyl formamide, and the like. The choice of solvents is such as to insure solubility of the ligand, the metal salt or both.

Typically, the compounds of the present invention are recovered by fractional crystallization, by precipitation with cosolvents, or by evaporation; however, other known techniques like decanting, filtration and the like, can also be used.

Compounds of the present invention are useful as oxidation catalysts. Indeed, one of the advantages of the compounds of the present invention is the presence of oxidation resistant ligands. Indeed, the fluoroalkyl groups near the metal center of the compound provide electron withdrawing groups to the metal center, and may have the resistance of the catalyst toward self-destructive decomposition.

The invention will be further illustrated in the following examples:

EXAMPLE 1

Preparation of $[CoL_f(NO_3)(CH_3CN)]$

Figure 1:
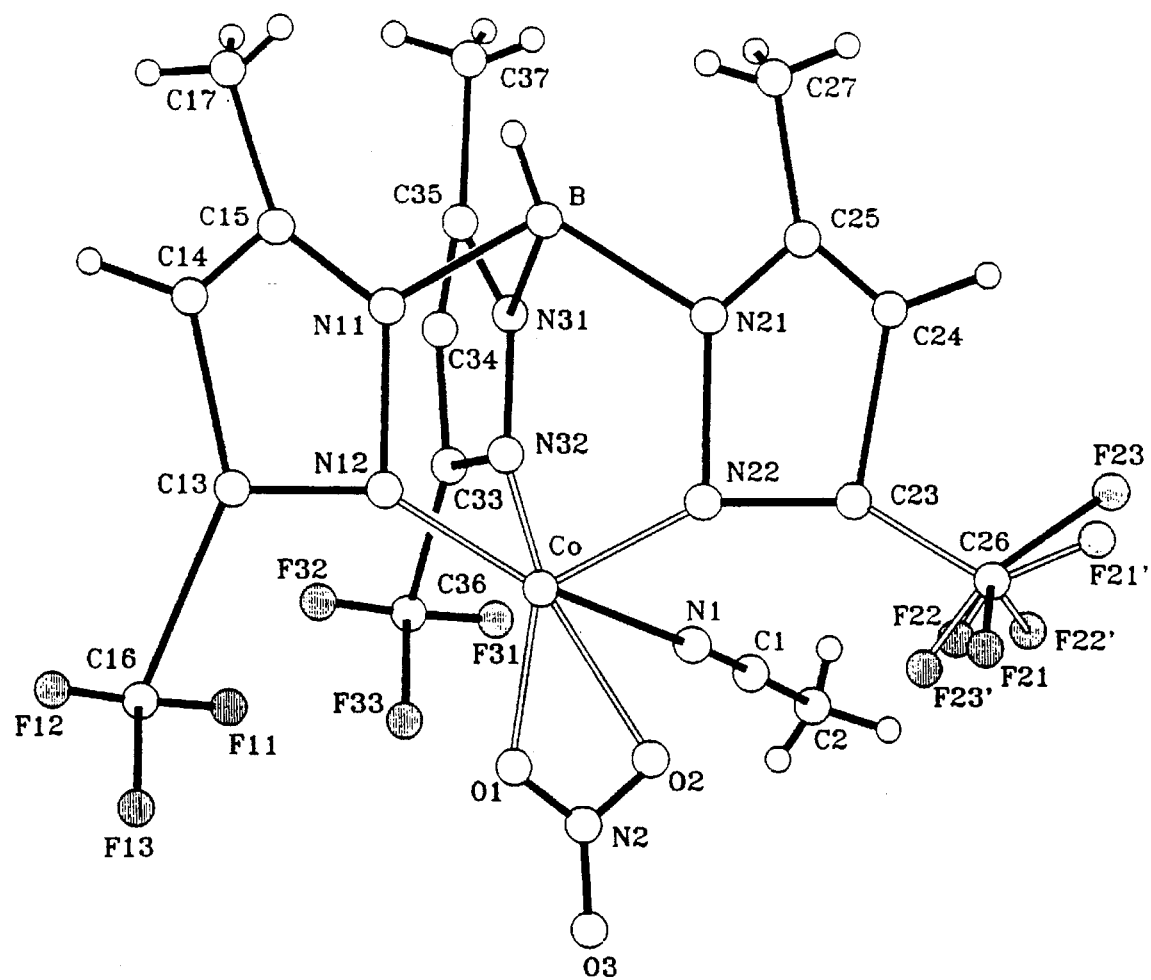
FIG. 1 is a perspective drawing of one complex of the invention, $Co[(C_5H_4N_2F_3)_3BH](NO_3)(NCCH_3)$, with all non hydrogen atoms represented by thermal vibration ellipsoids drawn to encompass 50% of their electron density, and hydrogen atoms arbitrarily represented by small spheres. In the figure, one of the $CF_3$ groups is shown to have 2 alternate orientations about the $(C_{23}$–$C_{26})$ C—$CF_3$ bond in the lattice. The major (68%) orientation for the fluorine atoms is represented by solid C—F bonds and specified by atoms $F_{21}$, $F_{22}$ and $F_{23}$; the minor (32%) orientation is represented by open C—F bonds and specified by atoms $F_{21}'$, $F_{22}'$, and $F_{23}'$.

To a 10 ml acetonitrile solution of 40 mg ($0.14 \times 10^{-3}$ moles) $Co(NO_3)_2 \cdot 6H_2O$ were added 60 mg ($0.12 \times 10^{-3}$ moles) of solid $KL_1$. After 10 minutes of stirring, the solution was filtered and red-purple crystals were isolated and characterized by single crystal X-ray diffraction. The structure is shown in FIG. 1.

EXAMPLE 2

Preparation of $[CoL_1Cl]$

To 10 ml acetonitrile solution of 40 mgs ($0.17 \times 10^{-3}$ moles) of $CoCl_2 \cdot H_2O$, 60 mgs ($0.12 \times 10^{-3}$ moles) of solid $KL_1$ was added. After stirring for 10 minutes, red-purple crystals were obtained by slow evaporation.

EXAMPLE 3

Preparation of $Cu(L_2)_2$

Figure 2:
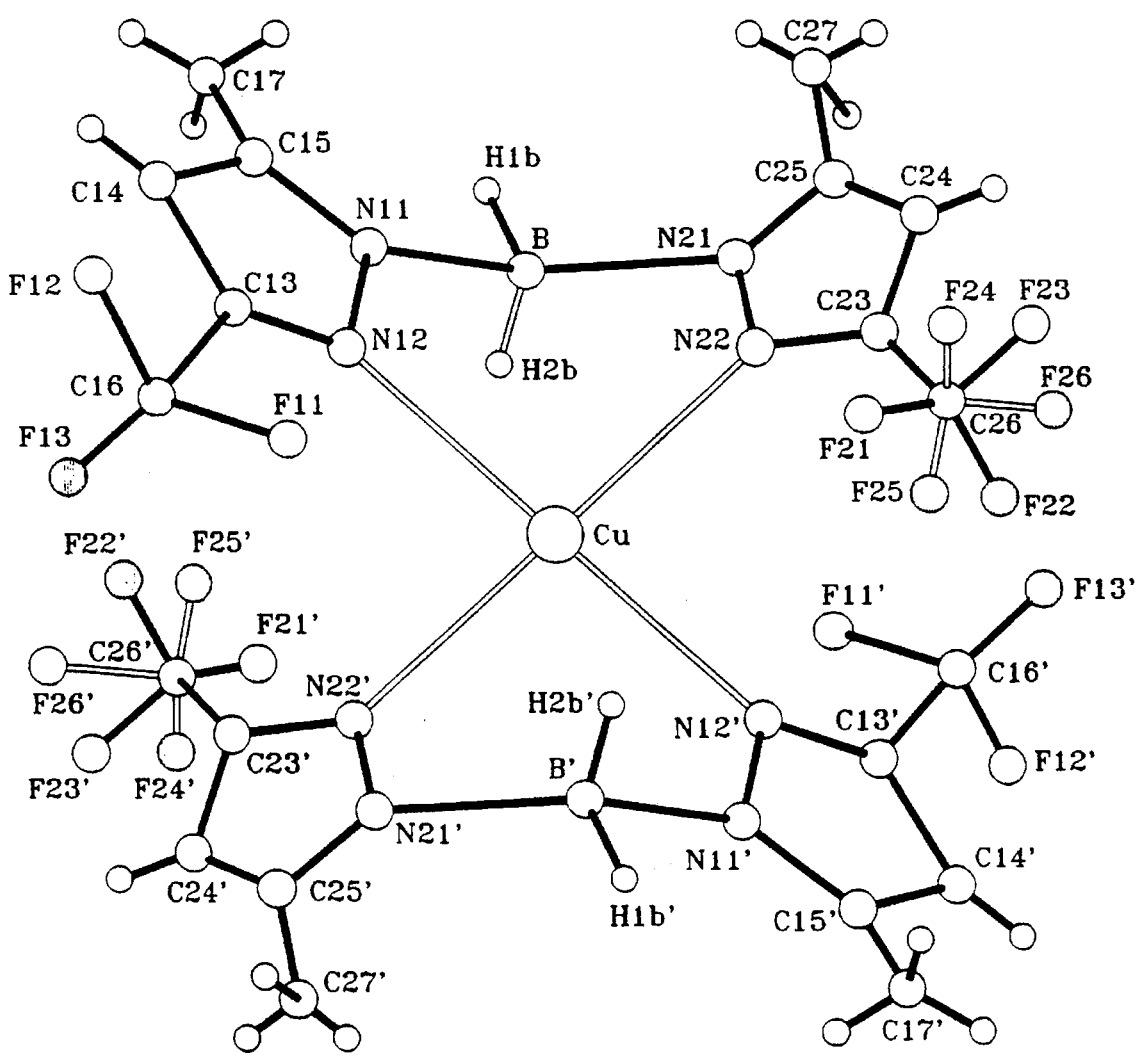
FIG. 2 shows a perspective drawing of another complex of the present invention, $Cu[(C_5H_4N_2F_3)_2BH_2]_2$, with non hydrogen atoms represented by thermal vibration ellipsoids drawn to encompass 50% of their electron density and hydrogen atoms arbitrarily represented by small spheres. One of the $CF_3$ groups per ligand is shown to have 2 alternate orientations in the lattice. The major (85%) orientation for the fluorine atoms is specified by atoms $F_{21}$, $F_{22}$ and $F_{23}$ (represented by solid C—F bonds) and the minor (15%) orientation is specified by $F_{24}$, $F_{25}$ and $F_{26}$ (represented by open C—F bonds).

To a 20 ml acetone solution of 400 mg ($1.08 \times 10^{-3}$ moles) of $Cu(ClO_4)_2 \cdot 6H_2O$ were added 760 mg ($2.17 \times 10^{-3}$ moles) of $KL_2$. After stirring for 10 minutes 60 mg ($1.08 \times 10^{-3}$ moles) of KOH was added and the mixture stirred for an additional 20 minutes. Addition of 5 ml of toluene followed by slow evaporation resulted in dark purple crystals which were structurally characterized by single crystal X-ray diffraction. The structure is shown in FIG. 2.

EXAMPLE 4

Preparation of $Cu(L_2)_2$

The procedure of Example 3 was repeated but without adding KOH. The stone product as in Example 3 was obtained.

EXAMPLE 5

Preparation of $[MnL_1(ClO_4)_2] \cdot n(CH_3CN)$

To a 10 ml acetonitrile solution of 45 mg ($0.095 \times 10^{-3}$ moles) $Mn(ClO_4)_2 \cdot 6H_2O$ was added 65 mg ($0.09 \times 10^{-3}$ moles) $KL_1$. The mixture was stirred at room temperature for 15 minutes and filtered. Colorless crystals of the title complex were obtained by evaporation.

EXAMPLE 6

Oxidation of cyclohexane by $[CoL_1(NO_3)(CH_3CN)]$

This example illustrates the use of a metal complex of the invention as an oxidation catalyst.

To 10 ml of cyclohexane 1 ml 80% cumyl hydroperoxide in cumene was added, followed by 10 mgs. of $[CoL_1(NO_3)(CH_3CN)]$ dissolved in 5 ml acetonitrile. After stirring for 24 hours at room temperature, GC analysis of the reaction mixture indicated the formation of cyclohexane and cyclohexanone. Cumyl hydroperoxide decomposition products were also observed.

What is claimed is:

1. A composition of matter having the $M_xL_yP_z \cdot nQ$ where M is a metal ion selected from the group consisting of Co, Ni, Zn, Mn, Cr, Zr, Ti, Hf, V and Fe; L is a fluoroalkyl substituted tris or bis pyrazole borate ion, or mixture thereof; P is a counterion; x, y and z are integers sufficient to render the composition electronically neutral; Q is a solvent; and n is a numerical value of from 0 to about 12.

2. The composition of claim 1 wherein Q is selected from the group consisting of water, alcohols of from 1 to about 12 carbon atoms, acetonitrile, and acetone.

3. The composition of claim 2 wherein L has the formula:

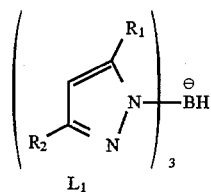

wherein $R_1$ is an alkyl group of from 1 to 12 carbon atoms or an aryl or aralkyl group of from 6 to 12 carbon atoms and $R_2$ is a fluoroalkyl group of from 1 to 12 carbon atoms.

4. The composition of claim 2 wherein L has the formula:

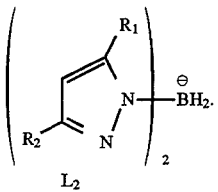

5. A method for forming a compound of the formula $M_xL_yP_z \cdot nQ$ where M is a metal ion selected from the group consisting of Co, Ni, Zn, Mn, Cr, Zr, Ti, Hf, V and Fe; L is a fluoroalkyl substituted tris or bis pyrazole borate ion, or mixture thereof; P is a counterion; x, y and z are integers sufficient to render the composition electronically neutral; Q is a solvent; and n is a numerical value of from 0 to 12 comprising:

combining a solution of an alkali metal salt of L, and a solution of a salt of M and recovering the compound.

6. The method of claim 5 wherein the alkali-metal of the salt of L is potassium.

7. The method of claim 6 wherein the salt of M is selected from chlorides, bromide, fluorides, nitrates, sulfonates, alkyl or aryl sulfonates, fluoroborates, phenyl borates, perchlorates and carboxylates.

8. The method of claim 7 wherein L has the formula:

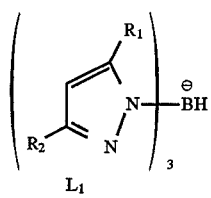

wherein $R_1$ is an alkyl group of from 1 to 12 carbon atoms or an aryl or aralkyl group of from 6 to 12 carbon atoms and $R_2$ is a fluoroalkyl group of from 1 to 12 carbon atoms.

9. The method of claim 7 wherein L has the formula:

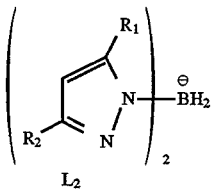

wherein $R_1$ is an alkyl group of from 1 to 12 carbon atoms or an aryl or aralkyl group of from 6 to 12 carbon atoms and $R_2$ is a fluoroalkyl group of from 1 to 12 carbon atoms.

* * * * *